United States Patent [19]

Boeing et al.

[11] 4,259,186

[45] Mar. 31, 1981

[54] GEL FILTRATION COLUMN

[75] Inventors: Joseph Boeing, Darmstadt; Hermann A. Mueller, Darmstadt-Arheilgen, both of Fed. Rep. of Germany

[73] Assignee: Röhm GmbH, Darmstadt, Fed. Rep. of Germany

[21] Appl. No.: 11,879

[22] Filed: Feb. 13, 1979

[30] Foreign Application Priority Data

Feb. 25, 1978 [DE] Fed. Rep. of Germany ....... 2808154

[51] Int. Cl.³ ............................................. B01D 15/08
[52] U.S. Cl. ................................. 210/198.2; 55/386; 210/286
[58] Field of Search ................ 210/31 C, 198 C, 286; 55/386

[56] References Cited

U.S. PATENT DOCUMENTS

| | | | |
|---|---|---|---|
| 2,253,685 | 8/1941 | Burckhlater | 210/286 X |
| 3,298,527 | 1/1967 | Wright | 210/198 C |
| 3,586,626 | 6/1971 | Heitz et al. | 210/31 C |
| 3,856,681 | 12/1974 | Huber | 210/198 C |
| 3,954,608 | 5/1976 | Valentin | 210/198 C |

*Primary Examiner*—John Adee
*Attorney, Agent, or Firm*—Curtis, Morris & Safford

[57] ABSTRACT

What is disclosed is an elongated gel filtration column having an outer wall and at least one gel chamber defined therein and adapted to be filled with a filter gel, said gel chamber being subdivided by a plurality of interior partition walls arranged parallel to the column wall, said partition walls being of a length shorter than the length of the gel chamber.

5 Claims, 3 Drawing Figures

GEL FILTRATION COLUMN

The present invention relates to an improved gel filtration column.

On a laboratory scale, gel filtration is a simple and reliable method for separating relatively small quantities of aqueous solutions which contain high molecular weight substances, for instance proteins, and low molecular weight substances, for instance salts, into their components. If the solution to be separated and the eluting agent subsequently used are introduced uniformly, sharply defined fractions of the components, of decreasing molecular weight, contained in the mixture of substances charged into the column can as a rule be eluted.

The translation of the process to an industrial scale in which kilogram quantities of mixtures of substances in the form of aqueous solutions are to be separated frequently gives considerable difficulties. The flow capacity, which is dependent on the density of filling of the gel column and on the viscosity and the quantity of the solution to be separated which is charged to the column, decreases with increasing column cross-section as a result of increasing compaction of the gel filling. At the same time the separation behavior changes. Since a uniform flow of liquid is indispensable in order to obtain a sharp, reproducible fractionation of the mixture of substances, both the solution to be separated and the eluting agent are generally pumped into the column at a constant rate of flow. If the fluid permeability of the gel filling drops below the delivery capacity of the pump, a static liquid pressure is developed in the entrance chamber of the column which further compacts the gel and further reduces its permeability. At this point, the process must be interrupted and the gel filling returned to its original condition by a time-consuming process.

Such disturbances in operation can be avoided, or at least delayed, if the column filling is subdivided into a plurality of flat layers. However, the sharpness of the fractionation is reduced by this. Furthermore the apparatus required becomes larger and more expensive and charging it with fresh gel and removing spent gel become more difficult. This is true to an even greater extent if a large number of thin columns connected in parallel are used instead of one column of large cross-section.

Further measures for reducing these disadvantages are dilution of the solution to be treated in order to reduce its viscosity and reduction of the amount and of the velocity of flow. All of these measures decrease the total output of the column.

A chromatography column consisting of a plurality of thin layers of the chromatographic separation material which lie parallel to the axis of the column is known in the prior art. The individual layers are separated from each other by inert plastic or metal foils. The height of the column is determined by the length of the separation foils, i.e. the filling of the column is exactly flush with the upper and lower edge of the separating foils at the upper and lower ends of the column, respectively. Aside from the cumbersome method of manufacture of the column, in which a foil coated with the chromatographic filling material is wound to form a column, it is difficult to assure a uniform filling of gel in all vertical segments of the column. As a result, there are non-uniform separation conditions in the vertical column segments, resulting in a correspondingly reduced sharpness of separation.

The object of the present invention is to create a gel filtration column for operation on an industrial scale, the permeability of which column to liquid does not decrease even upon continuous operation and which column permits separation behavior corresponding to that on a laboratory scale at the same output per unit of surface. The column, furthermore, is to be simple in construction and easy to fill and empty. This object is achieved by the gel filtration column of the invention.

A better understanding of the invention and of its many advantages will be had by referring to the accompanying drawings, in which FIG. 1 is a side view, in vertical section through the central plane of a column according to the invention;

Figure 1:
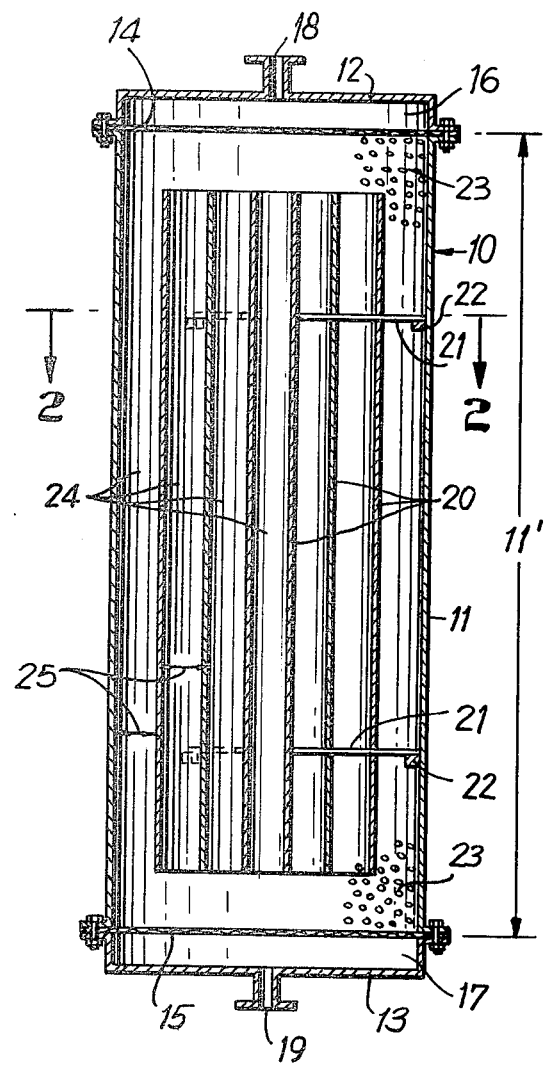

FIG. 1 shows column 10 comprising gel chamber 11, detachable column top 12, and detachable column bottom 13, all shown in the Figure as made of metal, but which may be made of any other suitably rigid inert material such as glass or plastic. Detachable perforated trays 14 and 15, also of metal or other inert material, respectively separate top 12 and bottom 13 from gel chamber 11 and define inlet chamber 16 and outlet chamber 17 with top 12 and bottom 13, respectively. Supply conduit 18 in top 12 communicates with inlet chamber 16 and discharge conduit 19 communicates with outlet chamber 17.

Figure 2:
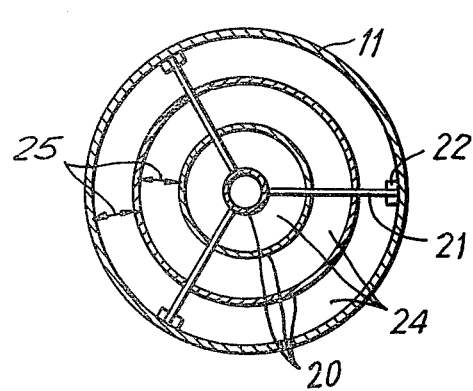
FIG. 2 is a plan view, in section, along line 2—2 of FIG. 1.

As also shown in FIG. 2, within column 10 are plurality of partition walls 20 suitably connected together by supports 21 to form a firm structural unit which can be removed from column 10 as a unit. The outermost ends of supports 21 suitably rest on brackets 22 affixed to the interior wall of gel chamber 11 to suspend the unit within the gel chamber. Supports 21 can be formed as individual narrow elements as shown in FIGS. 1 and 2, but can also themselves be formed as continuous partition walls. Again, all these elements are suitably of metal or some other inert material.

Partition walls 20 are shorter than gel chamber 11 so that gel filling 23 extends or protrudes above and below the ends of portion walls 20. (Gel filling 23 fills all portions of gel chamber 11 between perforated trays 14 and 15, but only a portion of the filling is shown in FIG. 1 in order not to obscure details of the column arrangement.) A difference in length between partition walls 20 and gel chamber 11 of from 4 to 20 percent, and preferably of about 10 percent, of height 11' of gel chamber 11 is as a rule the most advantageous. As a result, process conditions are created in vertical column segments 24, defined between walls 20 and between the outermost partition wall and the wall of column 10, which correspond in all segments 24, which in turn assure a uniform separation in each segment and thus a high sharpness of separation.

In order to make the conditions in all vertical segments 24 as uniform as possible, partition walls 20 are spaced apart from each other and from the column wall by spacings 25 which are as uniform as possible. The required spacings depend somewhat on the size of the gel particles: fine particles require smaller spacings while larger particles permit larger spacings. In general, the spacings are from 20 to 120 mm and preferably from 40 to 80 mm. It is sufficient if these spacings are maintained between the walls—no further subdivision is necessary along the length of walls 20.

Figure 3:
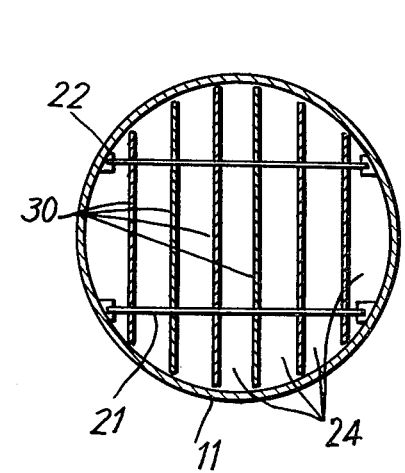
FIG. 3 is a similar plan view, in section, of another embodiment of the column of the invention.

The arrangement of the partition walls depends on the external shape of column 10 and the expedience of manufacture. Concentric tubes as shown in FIGS. 1 and 2 for walls 20 or parallel stacked plates 30 (cf. FIG. 3) are as simple as they are suitable.

The partition walls arranged in the gel chamber of the column effectively prevent a compacting of the gel filling. Columns of any desired cross section and any desired height can be produced. A larger effective column height can be obtained at only a slightly increased expense also by connecting two or more columns in series. As the filling, the customary dextran gels, polyacrylic gels, or other gels are used.

The detachable nature of top 12, bottom 13, and of perforated trays 14 and 15 facilitates the charging and emptying of gel chamber 11. The gel material is generally introduced as a dry granulate and swells somewhat when the column is filled with water or the aqueous liquid to be used for the operation. (The performations in trays 14 and 15 are made smaller than the diameter of the swollen gel particles.) The amount of gel material introduced is preferably such that the swollen volume which it would assume in case of spatially unimpeded swelling would be somewhat larger than the free volume of the gel chamber. Thus, in its swollen condition, the gel filling is under a slight pressure which counteracts the tendency towards compacting of the filling. A uniform swelling pressure in all vertical segments is important, since only then is the separating action the same in all segments 24 and the sharpness of separation of the entire column high. Uniform swelling is assured by making partition walls 20 shorter than gel chamber 11. Small irregularities in the amounts of gel which are present in the individual segments automatically equalize each other when the gel filling spills over the upper edge of the partitions during the course of the swelling process.

When operating, the column is generally completely filled with liquid. The direction of flow during operation is as desired.

The gel filtration column of the invention is operated in two steps, in the same way as corresponding known apparatus. In the charging step, the aqueous solution which contains a mixture of substances of high and low molecular weight components is allowed to flow into the column while at the same time an equal quantity of the original liquid filling is removed. This is followed by elution, during which the components of the solution having the highest molecular weight are eluted first. When the lowest molecular weight components have been completely eluted, a new operating cycle, consisting of a charging step and an elution step, can be started.

In order to counteract any gradual compacting and in order to maintain, for an unlimited time, unchanged operating conditions, even over a large number of operating cycles, it is advisable to reverse the direction of the flow after each operating cycle since the column gives the same results in both directions of flow.

What is claimed is:

1. An elongated gel filtration column having an outer wall and opposed inlet and outlet ends, said outer wall defining at least one gel chamber adapted to be filled with a filter gel, a pair of perforated trays respectively secured to said wall at said inlet and outlet ends, and inlet and outlet chambers respectively secured to said outer wall at said inlet and outlet ends in communication with said gel chamber through said perforated trays, said gel chamber being subdivided by a plurality of interior longitudinally extending partition walls arranged parallel to each other, said partition walls being of a length which is shorter than the length of the gel chamber and having free ends respectively inwardly spaced from said trays whereby the filter gel in said filter chamber is located between said partition walls and in the space between the ends of said walls and said trays and is subjected to substantially uniform pressure throughout the column.

2. A gel filtration column as in claim 1, wherein said plurality of partition walls are spaced from each other and from the column wall by distances of from 20 mm to 120 mm.

3. A gel filtration column as in claim 2 wherein said plurality of partition walls are spaced from each other and from the column wall by distances of from 40 mm to 80 mm.

4. A gel filtration column as in claim 1 wherein said plurality of partition walls are present in said column as concentric tubes.

5. A gel filtration column as in claim 1 wherein said gel chamber is filled with a filter gel in an amount such that the volume of the filter gel, when swollen, is greater than the free volume of the gel chamber.

* * * * *